United States Patent
Pringle

(10) Patent No.: US 6,505,498 B2
(45) Date of Patent: Jan. 14, 2003

(54) APPARATUS FOR DETERMINING A REPRESENTATIVE SPRING CONSTANT OF A GOLF CLUB HEAD

(75) Inventor: Matthew M. Pringle, Philadelphia, PA (US)

(73) Assignee: United States Golf Association, Far Hills, NJ (US)

( * ) Notice: Subject to any disclaimer, the term of this patent is extended or adjusted under 35 U.S.C. 154(b) by 0 days.

(21) Appl. No.: 09/853,178

(22) Filed: May 10, 2001

(65) Prior Publication Data
US 2002/0166363 A1 Nov. 14, 2002

(51) Int. Cl.⁷ ................................................ G01N 3/40
(52) U.S. Cl. ..................................................... 73/12.04
(58) Field of Search ........................... 73/12.01, 12.02, 73/12.04, 65.01, 65.07, 65.08, 65.09, 161

(56) References Cited
U.S. PATENT DOCUMENTS
4,062,222 A * 12/1977 Solheim ........................ 73/13
4,543,827 A * 10/1985 Tominaga et al. ............ 73/602

* cited by examiner

Primary Examiner—Benjamin R. Fuller
Assistant Examiner—Corey D. Mack
(74) Attorney, Agent, or Firm—Francis C. Hand; Carella, Byrne et al.

(57) ABSTRACT

The apparatus employs a steel ball which is mounted in upstanding manner on a pin and a frame on which a golf club is pivotally mounted to freely pivot. The golf club is pivoted from a fixed position to impact the head of a golf club against the steel ball and an oscilloscope is used to record the acceleration and movement of the steel ball from its fixed point in response to the impact of the head and also calculates a velocity history of the steel ball. The time at which the calculated velocity is at a maximum is determined. Several impacts are made to obtain an average characteristics time ($t_z$) and the representative spring constant ($K_c$) of the clubhead is calculated using the equation:

$$K_c = 0.2971 \times t_z^{-2.15570}.$$

21 Claims, 6 Drawing Sheets

APPARATUS FOR DETERMINING A REPRESENTATIVE SPRING CONSTANT OF A GOLF CLUB HEAD

This invention relates to an apparatus for determining a representative spring constant of a golf club head.

Appendix II, 5a of the Rules of Golf reads that the material and construction of, or any treatment to, the face or clubhead shall not have the effect at impact of a spring (test on file), or, in part, significantly more spin to the ball than a standard steel face, or have any other effect which would unduly influence the movement of the ball and, further, that the face of the club shall be hard and rigid (some exceptions may be made for putters) and, except for such markings listed below, shall be smooth and shall not have any degree of concavity.

Heretofore, various techniques have been employed to determine the effect at impact of a golf club head on a ball. One such procedure has been published by the United States Golf Association, Procedure for Measuring the Velocity Ratio of a Club Head for Conformance to Rule 5a, Appendix II, Revision 2, Feb. 8, 1999. This procedure, however, requires several steps and is relatively time consuming.

It is an object of this invention to simplify the test for determining the flexibility of a golf club head and in particular to measure a representative spring constant for a golf club head.

It is another object of the invention to determine a spring constant that is representative of the flexibility of a golf club head when impacted on the usual striking face.

It is another object of the invention to reduce the cost of testing to determine the flexibility of a golf club head.

It is another object of the invention to reduce the time required to perform a test for determining the flexibility of a golf clubhead.

It is another object of the invention to provide a portable apparatus for determining the flexibility of a golf club head.

Briefly, the invention provides an apparatus for estimating the flexibility of a golf club head.

The apparatus is comprised of a mass of material which is mounted at a fixed point and means for suspending a golf club having a head thereon from a fixed pivot point with the head disposed in opposition to the mass of material for freely pivoting of the golf club about the pivot point to impact the head against the mass of material. In addition, a means is provided for recording an acceleration in movement of the material mass from the fixed point in response to an impact of the golf club head on the mass and for calculating a velocity history of the material mass over time.

In one embodiment, the means for recording the acceleration of the material mass and calculating the velocity history includes an accelerometer which is connected to the mass for producing a voltage signal in dependence on the acceleration of the mass from the fixed point after being struck by the golf club head as well as an oscilloscope which is connected to the accelerometer to receive and record the voltage signal and to calculate the velocity history.

In another embodiment, a laser may be employed to detect the acceleration or velocity of the mass of material. For example, a laser may be used to determine the distance from the laser to the mass of material, e.g. a steel ball mounted on a shaft in a cantilevered manner, by determining the time that a pulse of light takes to reach the ball from the laser and bounce back to the laser. If this is done many times, the distances can be differentiated to calculate velocity and acceleration of the ball. Another embodiment could involve the use of a strain gauge on the shaft of the cantilevered ball.

As a matter of convenience, the apparatus includes a means for releasably holding the suspended golf club in a loading position with the head spaced from the mass of material. Once released, the golf club is free to pivot thereby allowing the head to move from a loading position against the material mass, for example, to fall in pendulum-like fashion into the mass of material.

In one embodiment, the apparatus includes a mounting block and a vertically upstanding column on a mounting block to support the mass of material thereon in a fixedly mounted manner. In this embodiment, the mass of material is made of steel of spherical shape.

The method provided by the invention allows for mounting the mass of material at a fixed point and of suspending the golf club from a fixed point with the head disposed in opposition to the mass of material for freely pivoting of the golf club to impact the head against the mass of material. In accordance with the method, the golf club is pivoted into a position to space the head from the mass of material and thereafter, the golf club is released to pivot under gravity to impact the head against the mass of material.

In accordance with the method, an acceleration of the mass of material is recorded during movement from the fixed point in response to the impact of the golf club head and a velocity history of the mass is calculated over time.

The recording and calculating steps are carried out by an oscilloscope or any other suitable means.

Further, in accordance with the method, the time at which the calculated velocity is at a maximum is determined. This time corresponds to the time at which the recorded acceleration is zero.

The method steps are repeated, for example, ten times, to obtain an average time ($t_z$). Thereafter, the representative spring constant ($K_c$) of the golf club head is estimated using the equation: $K_c = 0.2971 \times t_z^{-2.15570}$ where $t_z$ is the characteristic time in seconds and $K_c$ is the representative spring constant in N/m. Other forms of equations would be suitable.

These and other objects and advantages of the invention will become more apparent from the following detailed description taken in conjunction with the accompany drawings wherein.

Figure 7:
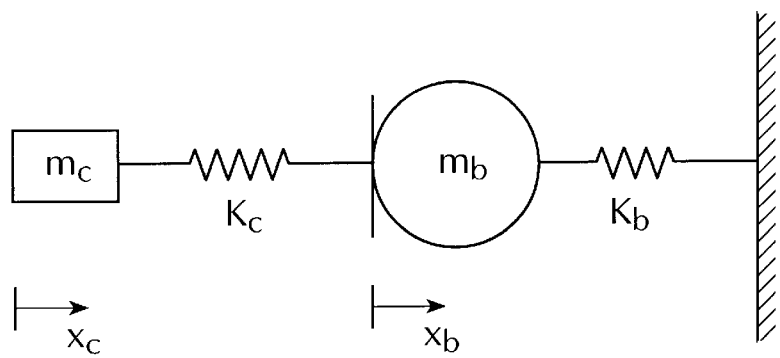
FIG. 7 illustrates an analytical model of an apparatus in accordance with the invention.

Referring to FIG. 7, it has been found that the impact of a club head with a ball may be adequately modeled by a simple two spring, two mass system as illustrated.

The equations of motion for this system are:

$$m_c \ddot{x}_c = -K_c(x_c - x_b)$$

$$m_b \ddot{x}_b = -K_b x_b + K_c(x_c - x_b)$$

Figure 8:
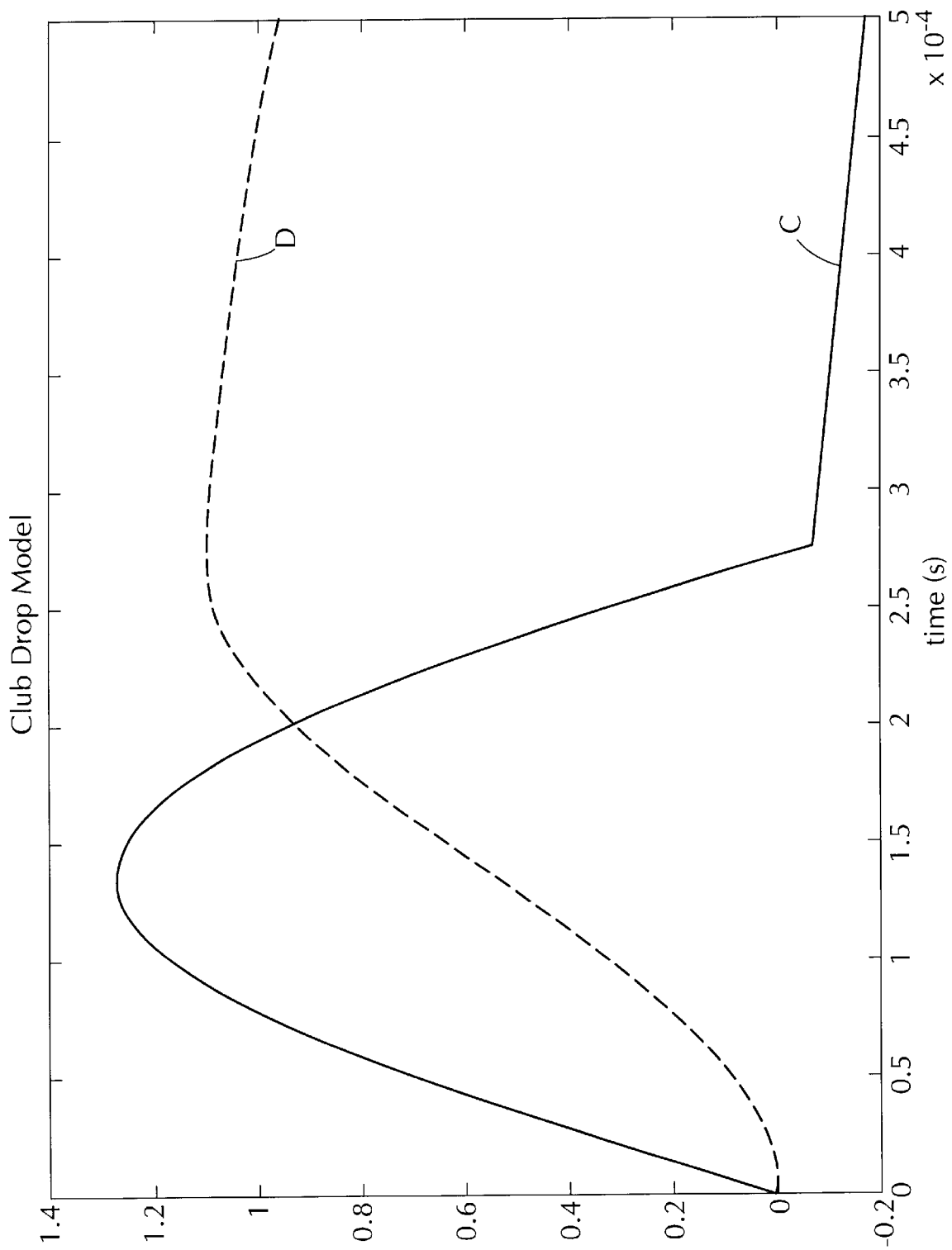
FIG. 8 illustrates a graph illustrating the acceleration and velocity of a ball in accordance with the analytical model.

The results of a numerical integration of the above two equations are illustrated in FIG. 8. One curve C represents the acceleration of the ball ($x_b$) and the other curve D represents the velocity of the ball ($V_b$), each relative to the time. The analytical model was used to determine the relationship between characteristic time ($t_z$) and representative spring constant ($K_c$) namely that $K_c=0.2971 \times t_z^{-2.15570}$.

Figure 1:
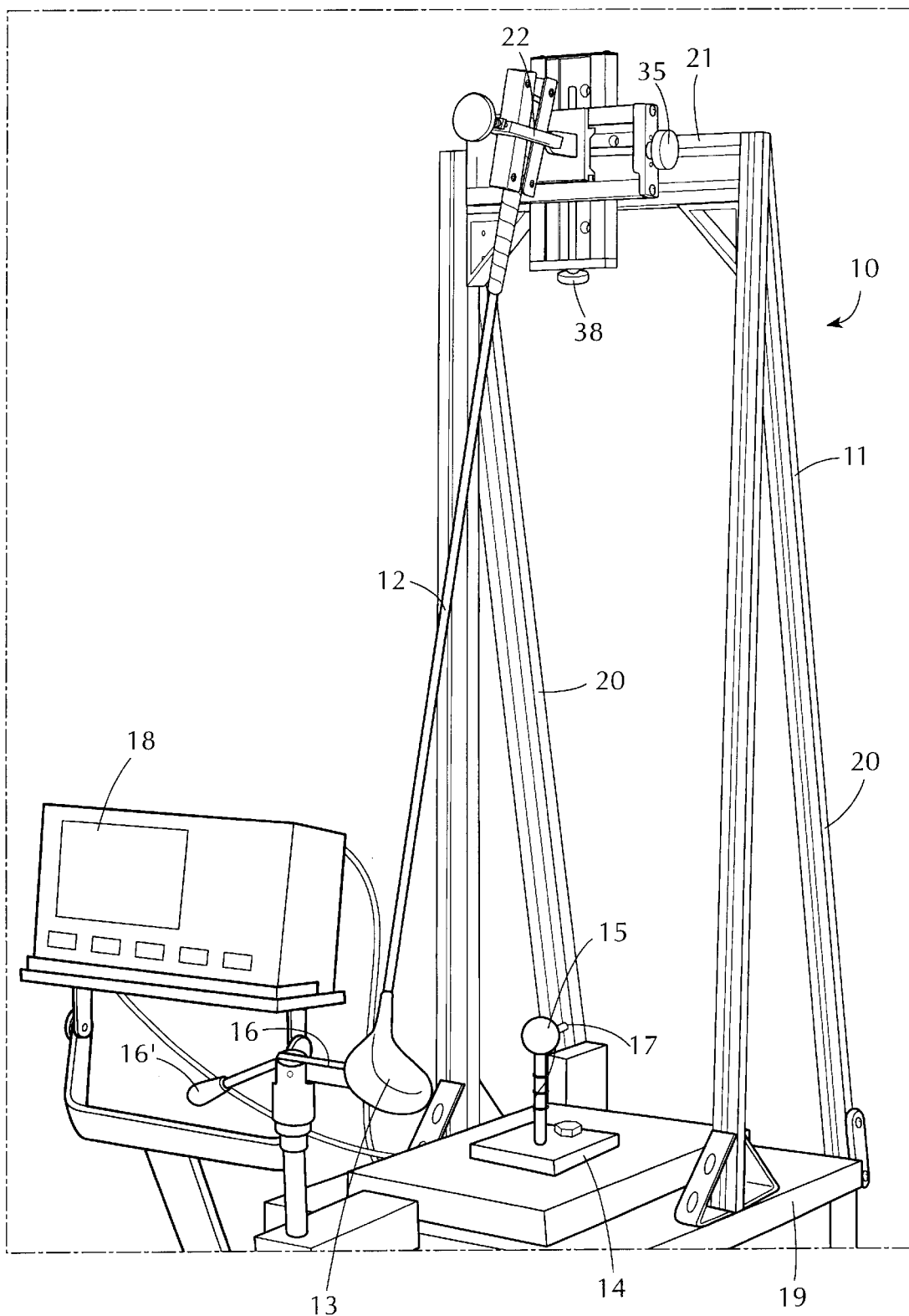
FIG. 1 illustrates a perspective view of an apparatus constructed in accordance with the invention.

Referring to FIG. 1, the apparatus 10 employs a means including an upstanding frame 11 for suspending a golf club 12 having a head 13 thereon from a fixed pivot point for freely pivoting of the golf club 12 about the pivot point. In addition, a mounting block 14 is positioned with the frame 11 in order to mount a mass of material 15 thereon in an upstanding cantilevered manner so that the mass of material 15 is disposed at a fixed point in a path of the head 13 of the golf club 12 suspended in the frame 11. A means 16 for releasably holding the suspended golf club 12 in a loading position is spaced in front of the frame 11 so that the head 13 can be spaced from the mass of material 15, for example, at a distance of 11.25 inches. Should a different distance be used, the coefficients in the above mentioned formula may be slightly different.

Still further, the apparatus employs means for detecting the acceleration or velocity of the mass of material 15. Such means may employ a laser as noted above or the like. In the illustrated embodiment, this means includes an accelerometer 17 which is connected to the mass of material 15 as described below and a means, such as, an oscilloscope 18 which is connected to the accelerometer 17 for purposes as described below.

The frame 11 is disposed on a support 19, such as a table which, in turn, may be readily movable from place to place for ease of transportation. As indicated, the frame 11 has a pair of inverted V-shaped and vertically disposed legs 20 secured to the support 19 and a horizontal cross bar 21 secured to and across the tops of the legs 20.

The means for suspending the golf club also has a grip holder 22 pivotally mounted on the cross bar 21 of the frame 11 in suitable fashion for holding the golf club 12 therein. The grip holder 22 is freely pivotal so that the golf club 12 may be swung in the matter of a pendulum and is more particularly described below.

The mounting block 14 is positioned between the vertical legs 20 of the frame 11. For example, the mounting block 14 is of relatively heavy weight and is made from plain carbon steel having dimensions of 12 inches by 18 inches and a thickness of 2 inches.

Figure 2:
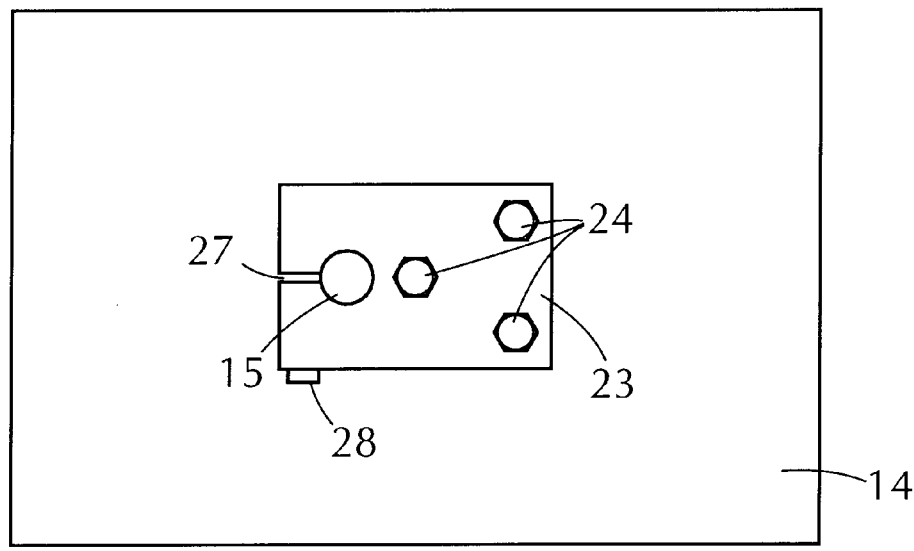
FIG. 2 illustrates a plan view of a means for mounting a steel ball of spherical shape in a fixed position in accordance with the invention.
Figure 3:
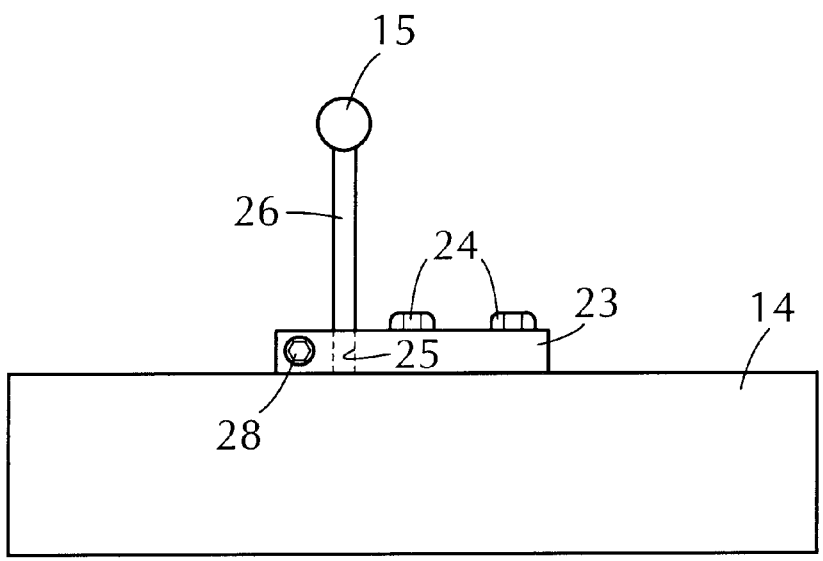
FIG. 3 illustrates a side view of the mounting means of FIG. 2.

Referring to FIGS. 2 and 3, the mounting block 14 has a plate 23 bolted thereon via suitable bolts 24. The plate 23 includes a bore 25 of circular shape for receiving a column, pin or the like 26 of carbon steel in vertically upstanding manner. In addition, a slot 27 (FIG. 2) extends from the bore 25 to split the plate 23 into two sections. A locking bolt 28 passes through one section of the plate 21 into a threaded bore (not shown) in the other section of the plate in order to close the slot 27 to tightly secure the upstanding column 26 to the plate 21 and thus to the mounting block 14.

As shown in FIGS. 2 and 3, the mass of material 15 is in the form of a spherical ball of steel fixedly secured to the top of the column 26.

Referring to FIG. 1, the means 16 for releasably holding the suspended golf club 12 in a loading position includes a unit that is secured in upstanding manner to the support. This unit is of conventional structure and need not be described in detail. For example, this unit includes a trip lever 16' that is pivotally mounted to move between an extended position as shown in FIG. 1 and a release position (not shown). When in the extended position, the trip lever 16' serves to hold the club head in a position of rest. When the trip lever is moved to the release position, the club head is released to swing toward the cantilevered steel ball. Actuation of the trip lever 16' is carried out manually although it is possible to do so mechanically or electrically.

Any suitable latch arrangement (not shown) is employed in order to hold the trip lever in the extended position.

Alternatively, the golf club may be manually pivoted from a vertically suspended position into a loading position and then released to swing under gravity against the mass of material. For example, a user may pivot the golf club to position the head a predetermined distance, such as, 11.25 inches, from the mass of material 15 and the may release the club for impact of the head on the mass of material 15.

Figure 4:
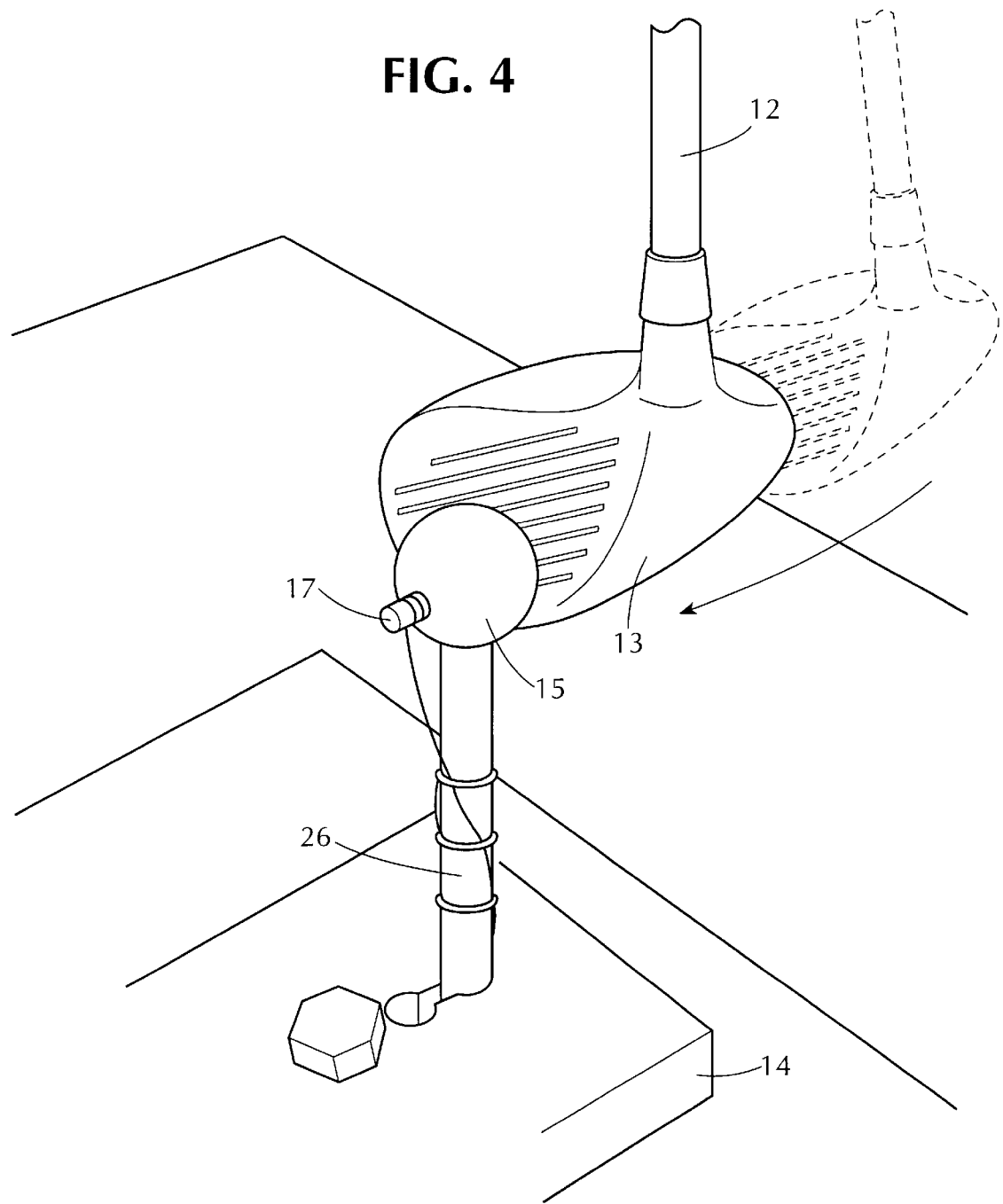
FIG. 4 illustrates a perspective view of a golf club head at a point of contact with the spherical ball in accordance with the invention.
Figure 6:
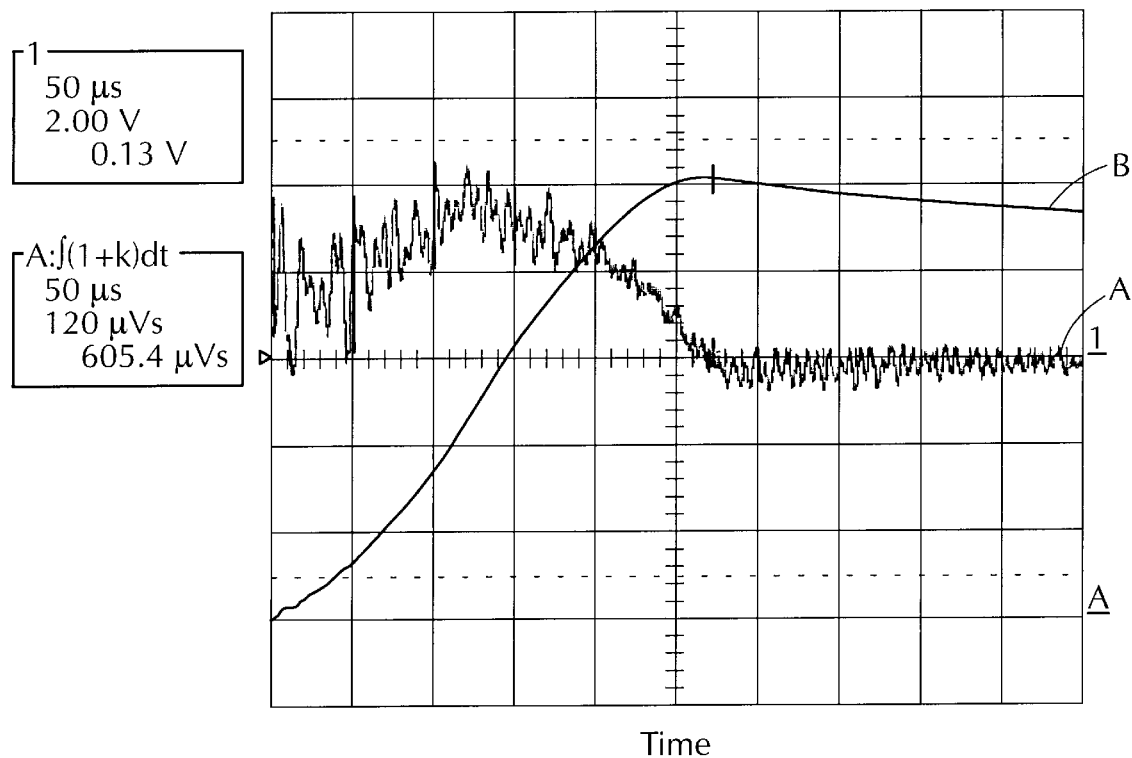
FIG. 6 illustrates an oscilloscope reading taken during an impact test in accordance with the invention.

Referring to FIG. 4, the accelerometer 17 is connected to the back of the cantilevered ball 15 and upstanding column 26 in a suitable manner in order to produce a voltage that depends on the acceleration of the ball 15 after being impacted by the club head 13, and to deliver a corresponding voltage signal to the oscilloscope 18 which records the signal, for example, as illustrated in FIG. 6 by the line A. In addition, the oscilloscope 18 or other suitable means is programmed to calculate a velocity history of the ball 15 over time as illustrated by curve B in FIG. 6 in dependence on the recorded acceleration.

Figure 5:
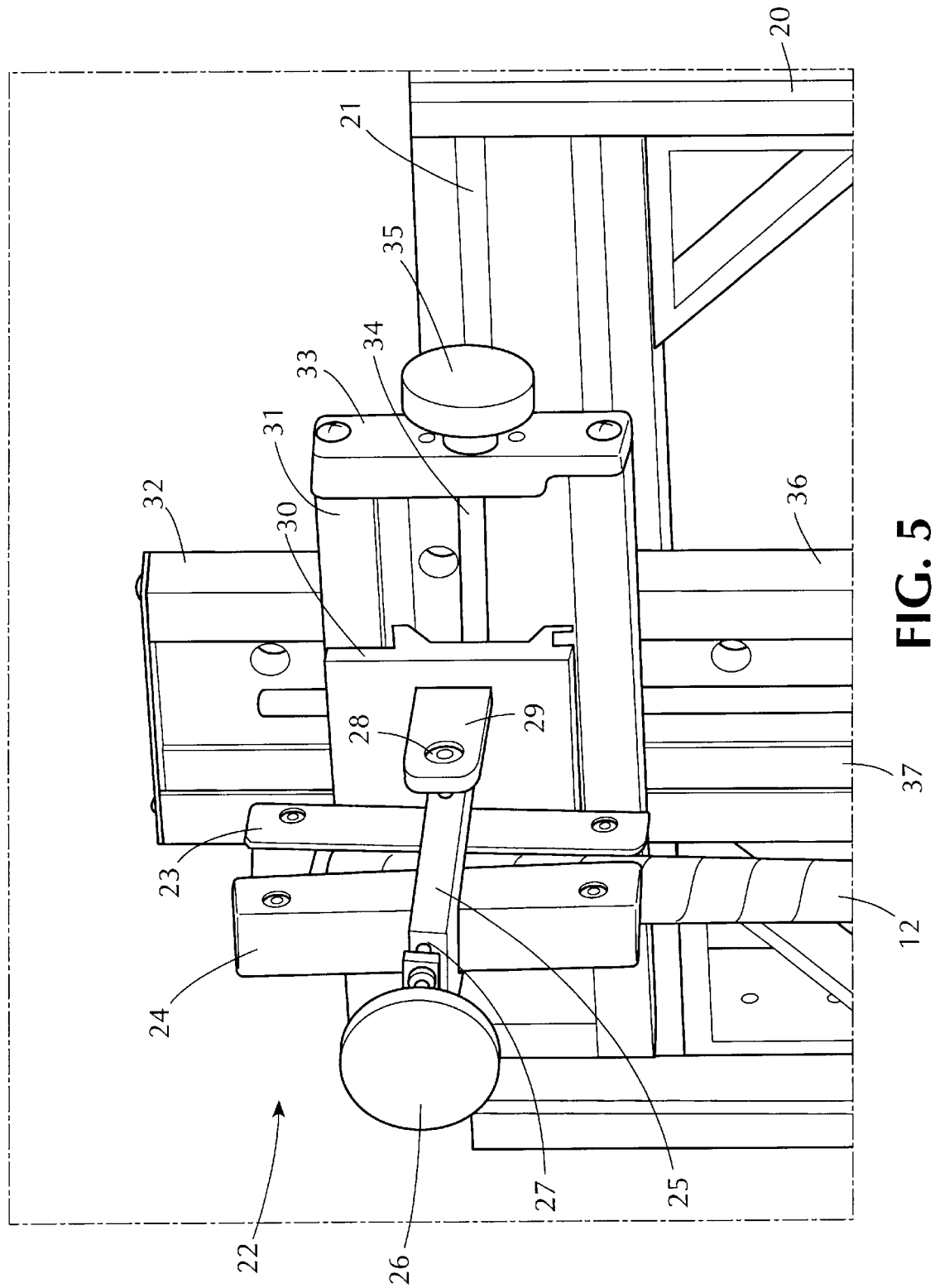
FIG. 5 illustrates a perspective view of a grip holder for gripping and suspending a golf club in accordance with the invention.

Referring to FIG. 5, the grip holder 22 is constructed to permit the head 13 of a golf club 12 to be positioned in contact with the face of the steel ball 15, for example, with the center of the head 13 in contact with the ball 15. To this end, the grip holder 22 includes a pair of clamping bars 23, 24 for gripping the golf club 12 therebetween. One of the clamping bars 23 is fixed secured between a pair of legs 25 of a U-shaped member while the other clamping bar 24 is movably mounted on and between the legs 25. In addition, a thumb screw 26 or the like is threaded into a cross bar of the bracket and is fixed to the movable clamping bar 24 on rotation of the thumb screw 26, the clamping bar 24 is movable relative to the fixed clamping bar 23 in order to grip or ungrip the golf club 12 therebetween. The U-shaped bracket 25, 27 is mounted on an axle 28 which, in turn, specifically mounted in a pair of ears 29 (only one of which is shown) on a mounting plate 30. The axle 28 is disposed on a horizontal axis which defines a fixed pivot point for the golf club 12.

As illustrated, the two clamping bars 23, 24 are of U-shaped cross section so as to receive the golf club 12 therein. A means 31 is provided for moving the bracket 30 along a horizontal axis to horizontally adjust the head 13 of the golf club 12 to the steel ball 15. In addition, a means 32 is provided for moving the bracket 30 along a vertical axis to vertically adjust the pivot point defined by the axial 29 relative to the steel ball 15.

As illustrated, the means 31 for moving the bracket 30 horizontally includes a frame 33 in which the bracket 30 is slidably mounted, a lead screw 34 which is rotatably mounted in the frame 33 and threadably mounted in the bracket 30 and a thumb screw 35 for rotating the leaf screw 34 in order to move the bracket 30 horizontally.

Likewise, the means for moving the bracket 30 vertically includes a frame 36, a lead screw 37 which is rotatably mounted in the frame 36 and threadably mounted on the frame 33 and a thumb screw 38 (see FIG. 1) for rotating the lead screw 37 in order to move the frame 33 vertically.

In order to test a golf club head to determine the representative spring constant of the club head, a golf club 15 secured to the grip holder 22 with the center of the face of the club head 13 contacting the cantilevered ball 15 as shown in FIG. 4. This is to position the geometric center of the club head 13 at the impact location. In order to ensure that the center of the face of the head 13 is properly positioned, a piece of carbon paper or any means of face marking, e.g. paint may be taped to the face of the club head 13 and the club 12 pulled back to the means 16 for releasably holding the head 13. After being released, the club head 13 would impact against the ball 15. The contact location is then visually checked to determine the point of impact. If the impact does not occur at the center of the head face, the golf club 12 is adjusted via the thumb screws 35, 38 and the procedure repeated until impact occurs at the center of the club face. Thereafter, the carbon paper is removed.

Once the club head 13 has been properly positioned, the club 12 is pivoted so that the head 13 is held by the trip lever of the means 16.

Next, the oscilloscope 18 is activated. The club head 13 is then released to freely pivot under gravity to impact against the ball 15. Because of the impact, the ball 15 moves from the fixed position thereof and subsequently returns to the fixed position. The oscilloscope 18 records the acceleration of the cantilevered ball as indicated by curve A in FIG. 6. At the same time, the oscilloscope 18 or any other suitable device calculates a velocity history of the ball 15.

As indicated in FIG. 6, the time at which the velocity of the ball 15 is a maximum corresponds to the time of zero acceleration of the cantilevered ball 15. This time is referred to as $t_z$.

The above steps are repeated, for example, ten times and an average $t_z$ is determined from the results.

Thereafter, the representative spring constant ($K_c$) may be calculated using the equation:

$$K_c = 0.2971 \times t_z^{-2.15570}$$

There is a close similarity of response between the experimental results illustrated in FIG. 6 and the analytical model as illustrated in FIG. 7.

The analytical model also indicates that the expression of the spring-mass system of the ball may take any form and need not be confined to a cantilevered steel ball as in the apparatus illustrated in FIGS. 1 to 3.

The invention thus provides a simple apparatus for easily and quickly determining the representative spring constant of a golf club head.

The invention further provides a device that is capable of determining a spring constant which is representative of the flexibility of a golf club head when impacted on the usual striking face of the club head.

The invention further provides an apparatus which may be readily transported from place to place.

What is claimed is:

1. An apparatus for measuring the representative spring constant of a golf club head, said apparatus comprising
   a mass of material mounted at a fixed point;
   means for suspending a golf club having a head thereon from a fixed pivot point with the head disposed in opposition to said mass of material for freely pivoting of the golf club about said pivot point to impact the head against said mass of material; and
   means for recording an acceleration in movement of said mass of material from said fixed point in response to an impact of the golf club head on said mass after the golf club head moves from a loading position to impact the head against said mass; and means for calculating a velocity history of said mass over time.

2. An apparatus as set forth in claim 1 wherein said for recording an accelaeration means includes an accelerometer connected to said mass for producing a voltage signal in dependence on an acceleration of said mass from said fixed point and an oscilloscope connected to said accelerometer to receive and record said voltage signal and to calculate said velocity history.

3. An apparatus as set forth in claim 2 wherein said mass of material is of spherical shape.

4. An apparatus as set forth in claim 3 which further comprises a mounting block and a vertically upstanding column mounted on said block and having said mass of material fixedly mounted thereon.

5. An apparatus as set forth in claim 1 wherein said mass of material is of spherical shape.

6. An apparatus as set forth in claim 1 wherein said means for suspending a golf club includes an upstanding frame and a grip holder for gripping a golf club mounted on said frame for pivoting about said pivot point and above said mass of material.

7. An apparatus as set forth in claim 6 wherein said grip holder includes a pair of clamping bars for gripping a golf club therebetween, a bracket pivotally mounting said clamping bars thereon for pivoting about said fixed pivot point, means for moving said bracket along a horizontal axis to horizontally adjust the head of a golf club to said mass of material and means for moving said bracket along a vertical axis to vertically adjust said pivot point relative to said mass of material.

8. An apparatus as set forth in claim 7 wherein said grip holder includes means for adjusting said clamping bars relative to each other to grip a golf club therebetween.

9. An apparatus as set forth in claim 1 which further comprises means for releasably holding the suspended golf club in said loading position with the head spaced from said mass of material.

10. An apparatus for measuring the representative spring constant of a golf club head, said apparatus comprising
    a frame for suspending a golf club having a head thereon from a fixed pivot point for freely pivoting of the golf club about said pivot point;
    a grip holder mounted on said frame for gripping a golf club for pivoting about said pivot point;
    a mounting block having a mass of material mounted thereon in an upstanding cantilevered manner, said mass of material being disposed at a fixed point in the path of a head of a golf club suspended from said grip holder;
    an accelerometer connected to said mass of material for recording an acceleration in movement of mass of material from said fixed point in response to an impact of the golf club head on said mass after moving from a position spaced from said mass to a position impacting against said mass; and
    means connected to said accelerometer to receive and record said voltage signal and to calculate a velocity history of said mass over time.

11. An apparatus as set forth in claim 10 wherein said mass of material is of spherical shape.

12. An apparatus as set forth in claim 10 which further comprises means for releasably holding the suspended golf club in a position spaced from said mass of material.

13. An apparatus as set forth in claim 10 wherein said mass of material is a steel ball.

14. An apparatus as set forth in claim 10 wherein said means is an oscilloscope.

15. An apparatus as set forth in claim 10 which further comprises a grip holder for gripping a golf club mounted on said frame for pivoting about said pivot point and above said mass of material.

16. An apparatus as set forth in claim 15 wherein said grip holder includes a pair of clamping bars for gripping a golf club therebetween, a bracket pivotally mounting said clamping bars thereon for pivoting about said fixed pivot point, means for moving said bracket along a horizontal axis to horizontally adjust the head of a golf club to said mass of material and means for moving said bracket along a vertical axis to vertically adjust said pivot point relative to said mass of material.

17. A method of determining a representative spring constant of a golf club head, said method including the steps of mounting a mass of material at a fixed point;

suspending a golf club having a head thereon from a fixed pivot point with the head disposed in opposition to the mass of material for freely pivoting of the golf club about said pivot point to impact the head against the mass of material;

pivoting the golf club to a position to space the head from the mass of material;

thereafter releasing the golf club from said position to freely pivot under gravity to impact the head against the mass of material;

recording the acceleration of the mass of material in movement from said fixed point in response to an impact of the golf club head on the mass;

calculating a velocity history of the mass over time in dependence on said recorded acceleration;

determining the time ($t_z$) at which the calculated velocity is at a maximum, said time corresponding to the time at which the recorded acceleration is zero;

repeating said steps to obtain an average time ($t_z$); and mathematically calculating the representative spring constant of the golf club head.

18. A method as set forth in claim 17 wherein said step of mathematically calculating the representative spring constant ($K_c$) uses the equation:

$$K_c = 0.2971 \times t_z^{-2.15570}.$$

19. A method as set forth in claim 17 wherein said steps are repeated a multiple of ten times to obtain said average time.

20. A method as set forth in claim 17 wherein said step of pivoting the golf club is conducted manually.

21. A method as set forth in claim 17 wherein the mass of material has a spherical shape and which further comprises the step of adjusting the golf club head relative to the mass of material to position the center.

* * * * *

UNITED STATES PATENT AND TRADEMARK OFFICE
CERTIFICATE OF CORRECTION

PATENT NO. : 6,505,498 B2
DATED : January 14, 2003
INVENTOR(S) : Matthew M. Pringle It is certified that error appears in the above-identified patent and that said Letters Patent is hereby corrected as shown below:

Column 1,
Line 10, change "in part" to -- impart --

Column 4,
Line 33, change "fixed" to -- fixedly --
Line 42, change "specifically" to -- is fixedly --
Line 67, before "secured" insert -- is --

Signed and Sealed this

Eighteenth Day of March, 2003

JAMES E. ROGAN
*Director of the United States Patent and Trademark Office*